US00PP18102P2

(12) United States Plant Patent
Lim

(10) Patent No.: US PP18,102 P2
(45) Date of Patent: Oct. 2, 2007

(54) GRANDIFLORA ROSE NAMED 'BAICENT'

(50) Latin Name: *Rosa hybrida*
Varietal Denomination: BAIcent

(75) Inventor: Peter P. Lim, McMinnville, OR (US)

(73) Assignee: Bailey Nurseries, Inc., Newport, MN (US)

( * ) Notice: Subject to any disclaimer, the term of this patent is extended or adjusted under 35 U.S.C. 154(b) by 2 days.

(21) Appl. No.: 11/408,348

(22) Filed: Apr. 21, 2006

(51) Int. Cl.
*A01H 5/00* (2006.01)

(52) U.S. Cl. ..... Plt./132

(58) Field of Classification Search ..... Plt./132, Plt./130
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of grandiflora rose, *Rosa* 'BAIcent', characterized by its clusters of double, high-centered blossoms on long, straight stems with apricot to pale yellow flowers that turn creamy white. Abundant flowers are present in May and June and recurrently throughout the season over dark green, satiny, bronze tinged foliage that is resistant to rose blackspot and powdery mildew. The new variety is readily propagated on its own roots and hardy in U.S.D.A. Zones 4 to 9.

2 Drawing Sheets

Botanical classification: *Rosa hybrida.*
Variety denomination: 'BAIcent'.

BACKGROUND OF THE INVENTION

The present invention relates to a new and distinct cultivar of *Rosa hybrida.* The new cultivar will be referred to hereafter by its cultivar name, 'BAIcent'. 'BAIcent' is a grandiflora rose suitable for use in garden plantings.

The new cultivar of rose is a selection from a controlled breeding program conducted by the inventor in Yamhill, Oreg. with a focus to create cultivars of roses with greater winter hardiness and improvements in disease resistance combined with good flower quality.

The new variety of rose, 'BAIcent', designated as seedling No. 96R815, was selected among seedlings derived from a cross made in Yamhill, Oreg. in 1996 between the female parent, 'MACivy' (U.S. Plant Pat. No. 8,362) and the male parent, designated No. R3412 (unnamed proprietary seedling, not patented). 'BAIcent' was selected as unique and budded onto understock in August 1997 and reselected by the inventor for its distinct characteristics in 2000.

The new cultivar has been asexually propagated by budding on an understock of 'Dr. Huey' (not patented) and by rooting of softwood cuttings. Asexual propagation in Yamhill, Oreg., St. Paul, Minn., and Litchfield, Ariz. by these techniques have determined that the characteristics of this cultivar are stable and are reproduced true to type in successive generations.

SUMMARY OF THE INVENTION

The following traits have been repeatedly observed and represent the characteristics of the new rose as observed for a period of five years in Yamhill, Oreg. and St. Paul, Minn. These attributes in combination distinguish 'BAIcent' as a unique cultivar of rose.

1. 'BAIcent' exhibits clusters of double, high-centered blossoms on long, straight stems with apricot to pale yellow flowers that turn creamy white when mature.

Flower color is classified as an apricot-blend by American Rose Society standards.

2. 'BAIcent' has dark green, satiny, bronze tinged foliage.
3. 'BAIcent' exhibits an upright oval shaped plant habit.
4. 'BAIcent' is a recurrent bloomer, blooming abundantly in May and June and then recurrently throughout the season.
5. 'BAIcent' has shown excellent resistance to rose blackspot (*Diplocarpon rosae*) and powdery mildew (*Sphaerotheca pannosa* var. *rosa*).
6. 'BAIcent' is hardy in U.S.D.A. Zones 4 to 9.
7. 'BAIcent' is a vigorous grower and readily propagated by softwood cuttings and grown on its own roots.

The new cultivar of rose can be readily distinguished from its parents and other cultivars. The female parent, 'MACivy', a floribunda, has flowers with a greater petal count that are pinker in coloration, exhibits a rounded plant habit and is everblooming. The male parent, Seedling no. R93412, a shrub rose, has light yellow colored semi-double flowers and lighter colored foliage. The cultivars 'Prairie Sunrise' (not patented) and 'Medallion' (not patented) are the closest comparison roses. They are both similar to 'BAIcent' in flower color, however 'Prairie Sunrise' is a shrub rose with larger, fuller flowers an lighter colored foliage and 'Medallion', a hybrid tea rose, is taller, has larger flowers and is everblooming.

BRIEF DESCRIPTION OF THE DRAWING

The accompanying colored photographs illustrate the overall appearance and distinct characteristics of the new rose, 'BAIcent', as grown outdoors in trial blocks and containers in St. Paul, Minn. and Yamhill, Oreg. The photographs were taken of two to three year-old plants grown own their own roots.

Figure 1:
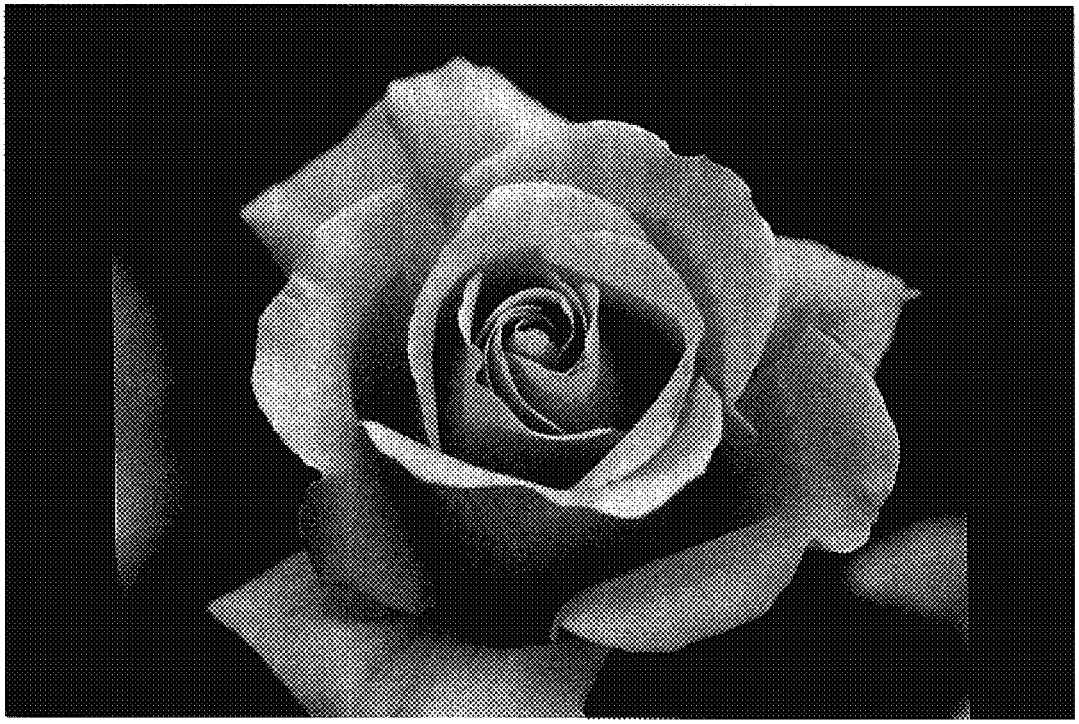
FIG. 1 provides a view a view of a flower just beginning to open.
Figure 2:
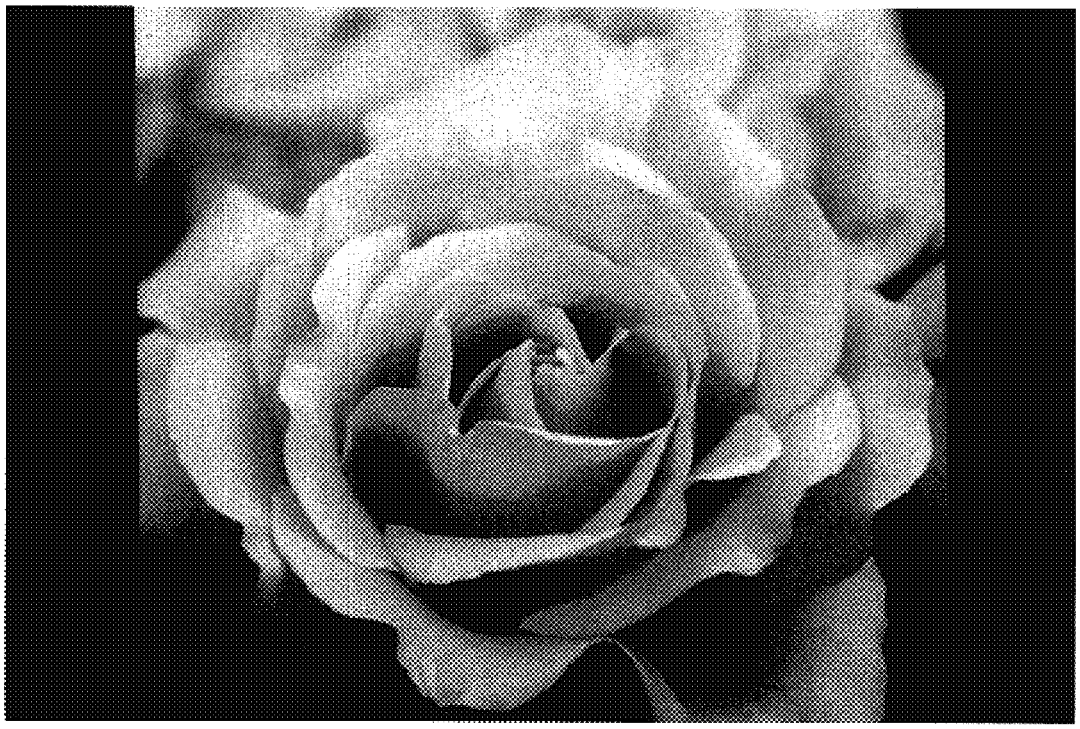
FIG. 2 provides a view of a flower almost fully open.
Figure 3:
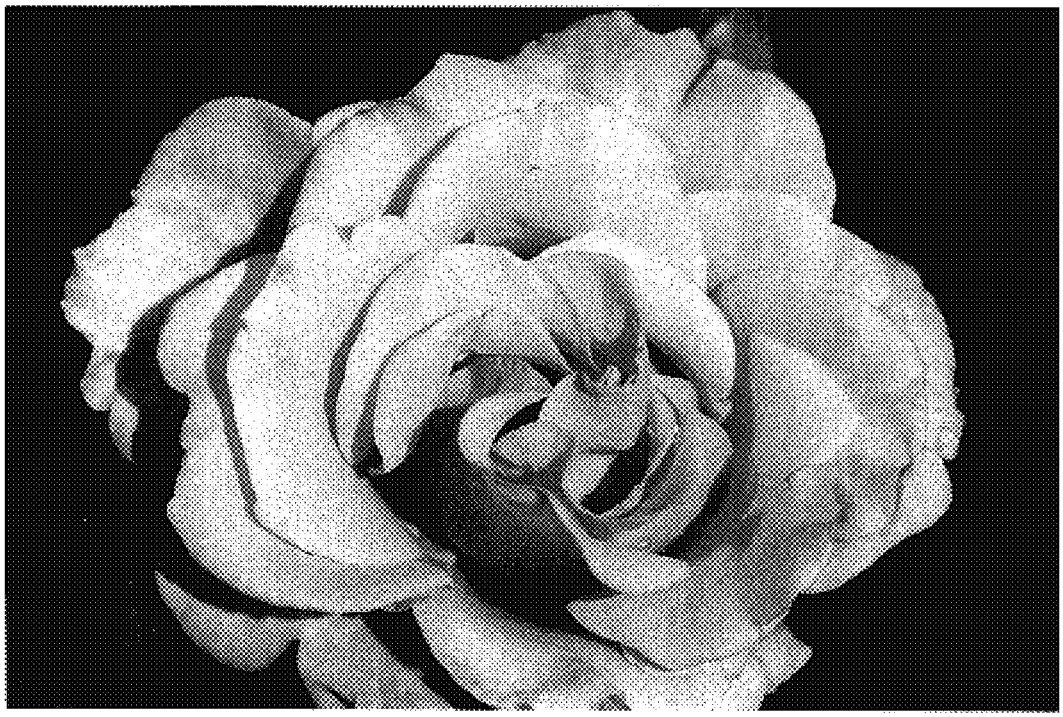
FIG. 3 provides a view of a fully open flower and a leaf.
Figure 4:
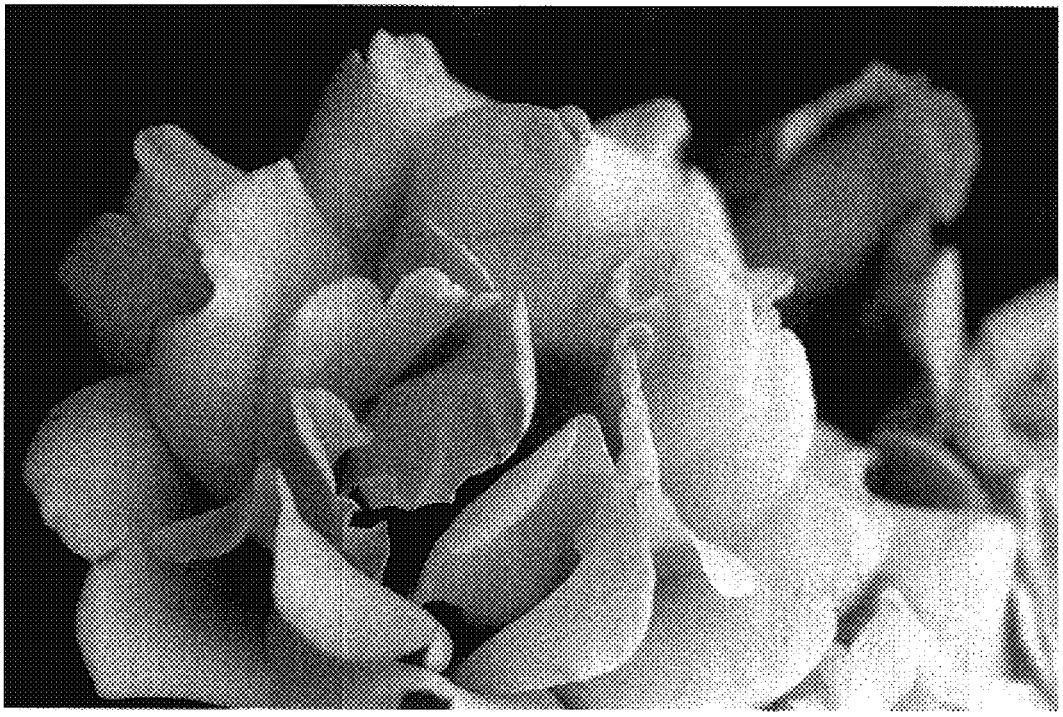
FIG. 4 provides a view of a mature flower.

The colors in the photographs are as close as possible with digital photography techniques available, the color values cited in the detailed botanical description accurately describe the colors of the new grandiflora rose.

DETAILED BOTANICAL DESCRIPTION

The following is a detailed description of the new cultivar as observed on two and three year-old plants grown outdoors under field conditions in Yamhill, Oreg. and St. Paul, Minn. The phenotype of the new cultivar may vary with variations in environmental, climatic, and cultural conditions, as it has not been tested under all possible environmental conditions. The color determination is in accordance with The R.H.S. Colour Chart of The Royal Horticultural Society, London, England, except where general color terms of ordinary dictionary significance are used.

General description:

*Botanical classification.*—*Rosa hybrida* 'BAIcent'.

*Parentage.*—Seed parent Rosa 'MACivy' (U.S. Plant Pat. No. 8,362), pollen parent No. R93412 (proprietary unnamed shrub rose seedling).

*Blooming habit.*—Abundant in May and June and recurrent throughout the growing season.

*Plant habit.*—Upright oval shaped plant habit.

*Height and spread.*—Reaches 60 to 90 cm in height and 80 cm to 90 cm in spread.

*Cold hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 144A suffused with 183B, maturing; between 138A and 138B, mature wood; 197A with spots showing through of 138A.

*Stem surface.*—Young; glabrous, adult wood; mostly glabrous with bark-like ridges.

*Thorns.*—Triangular and slightly curved in shape, oval base, average of 4 per 5 cm in number, an average of 9 mm in length with a base 8.8 mm in length and 2 mm in width, color is 185B suffused with 144B toward the tip.

Foliage description:

*Leaves.*—Division is odd-pinnate, average of 8.5 cm in length and 7.3 cm in width, internode length is an average of 5 cm.

*Leaflets.*—Average of 5 (range 3–5 or rarely 7), ovately oblong in shape, rounded to cuneate base, broadly acute apex, serrated margins, glabrous with satin sheen on upper and lower surface, average of 4.1 cm in length and 2.7 cm in width , color: young leaves upper surface; 144A, 144B, 146B and 146C suffused with color between 185A and 187B (purple is deeper on margin), young leaves lower surface; 146B and 146C suffused with 187B and 187C (purple is deeper on margin), mature leaves upper surface; 137A maturing to 147A suffused with 183B and 187B on blade and 187B on margin, mature leaves lower surface; between 146B and 147 suffused with 183B on blade and 187B on margin.

*Rachis.*—Average of 2.8 cm in length and 1.1 mm in diameter, color of upper surface 144A with 145A between ridges suffused with 182A, color of lower surface 144A.

*Stipules.*—Long and narrow with auricle facing outward, average of 1.6 cm in length and 0.5 mm in width, color of upper surface is 144A with stripes and solid areas of 146B on auricle and 182A on middle ridge, color of lower surface is the same as upper surface except closer to 146D near petiole.

*Petioles.*—Average of 2.2 cm in length and 1.3 mm in diameter, color of upper surface 144A with 145A between ridges suffused with 182A, color of lower surface 144A.

Inflorescence description:

*Inflorescence type.*—Corymbs of double flowers.

*Flower number.*—Average of 3 per lateral stem.

*Flower fragrance.*—Sweet rose scent.

*Flower longevity.*—About 3 to 5 days, depending on temperature and sunlight exposure.

*Flower type.*—Double, shallow cupped.

*Flower size.*—Average of 8.7 cm in diameter and 2.8 cm in depth.

*Peduncles.*—Stiff, average of 3.5 cm in length and 3.2 mm in diameter, surface is glabrous with some short hairs, color is color is 143B and 144A suffused with 144B.

*Flower buds.*—Ovate in shape (pointed), medium to large in size with an average of 2.7 cm in length and 1.6 cm in width prior to opening, color 13A and 13B suffused with 31A and 31B, texture is glabrous with some short hairs, mostly toward margins.

*Sepals.*—5, broadly lanceolate in shape, margin is entire and ciliate with outer 2 sepals having foliaceous appendages in pinnate pattern and center sepal having appendages on one side, color of upper and lower surface 144A suffused with 144C and 185A, upper surface is tomentose, lower surface is strigose, average of 3.1 cm in length and 6.8 mm in width, apex is apiculate on 2 inner sepals and leaf-like on the other 3, base is truncate, aspect is upright in bud stage changing to horizontal when bud opens and reflexed in full bloom.

*Petals.*—Average of 22, drop readily and cleanly, broadly obovate in shape and curled at apex, upper and lower surface is glabrous and satiny, entire margin, cuneate base, rounded to truncate apex, average of 3.8 cm (range 2.8 to 4.1) in length and 3.2 cm (range 2.7 to 3.5) in width, color: opening flowers upper surface; between 10A and 11A, opening flowers lower surface; 20A suffused with 31D, fully open flowers upper surface; between 11A and 11B, fully open flowers lower surface; between 16B and 16C with inner petals suffused with 22B, end of bloom upper surface; primarily 4D suffused with 155A, 4B and 5A, end of bloom lower surface; primarily 9D suffused with 9A and 10B, base petal spot; 13A.

*Receptacle.*—Average of 7.6 mm in diameter and 1.2 cm in depth when flower is fully open, urn shaped, glabrous with some glaucous coating, color is between 144A with streaks of 60A on the side exposed to sun.

*Pistils.*—Average of 75, stigma is an average of 1 mm in length, an average of 0.4 mm in width and 2A in color, style is an average of 4.3 mm in length and 46A in color suffused with 47B.

*Stamens.*—Average of 96, filaments are an average of 1.1 cm in length and 17B in color, anthers are an average of 2.4 mm in length, an average of 1.5 mm in width and 16B in color, pollen is 21B in color.

*Hips.*—None have formed under the trial conditions.

I claim:

1. A new and distinct cultivar of grandiflora rose plant named *Rosa* 'BAIcent' as herein illustrated and described.

* * * * *